United States Patent
Nakasone et al.

(10) Patent No.: US 10,168,295 B2
(45) Date of Patent: Jan. 1, 2019

(54) GAS SENSOR, METHOD OF PRODUCING CONDUCTIVE PASTE, AND METHOD OF MANUFACTURING GAS SENSOR

(71) Applicant: NGK INSULATORS, LTD., Nagoya-shi, Aichi (JP)

(72) Inventors: Osamu Nakasone, Inabe (JP); Takayuki Sakurai, Kakamigahara (JP); Satoshi Nishikawa, Chita (JP); Shotaro Niizuma, Kasugai (JP); Noriko Hirata, Nagoya (JP); Yuki Nakayama, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 46 days.

(21) Appl. No.: 14/800,171

(22) Filed: Jul. 15, 2015

(65) Prior Publication Data

US 2016/0033447 A1 Feb. 4, 2016

(30) Foreign Application Priority Data

Jul. 29, 2014 (JP) .................................. 2014-153418
Jun. 17, 2015 (JP) .................................. 2015-121843

(51) Int. Cl.
*G01N 27/407* (2006.01)
*G01N 27/30* (2006.01)
*H01B 1/02* (2006.01)

(52) U.S. Cl.
CPC ....... *G01N 27/4071* (2013.01); *G01N 27/301* (2013.01); *G01N 27/4075* (2013.01); *G01N 27/4076* (2013.01); *H01B 1/02* (2013.01)

(58) Field of Classification Search
CPC .............. G01N 27/406–27/41; G01N 27/4074
See application file for complete search history.

(56) References Cited

U.S. PATENT DOCUMENTS 5,902,469 A * 5/1999 Kato .................... G01N 27/419
                                                        204/425
5,989,624 A * 11/1999 Kida .................. G01N 27/4075
                                                        204/421

(Continued)

FOREIGN PATENT DOCUMENTS

DE         102005047443 A1    4/2007
DE    10 2008 042 770 A1      4/2010

(Continued)

OTHER PUBLICATIONS

The Extended European Search Report for the corresponding European patent application No. 151780723 dated Dec. 4, 2015.

(Continued)

*Primary Examiner* — J. Christopher Ball
(74) *Attorney, Agent, or Firm* — Global IP Counselors, LLP

(57) ABSTRACT

A sensing electrode for sensing a predetermined gas component of a measurement gas, which is provided in a mixed-potential gas sensor that measures the concentration of the predetermined gas component, is formed of a cermet containing a noble metal and an oxygen-ion conductive solid electrolyte. The noble metal comprises Pt and Au. An Au abundance ratio, which is an area ratio of a portion covered with Au to a portion at which Pt is exposed in a surface of noble metal particles forming the sensing electrode, is 0.3 or more.

15 Claims, 6 Drawing Sheets

(56) References Cited

U.S. PATENT DOCUMENTS

| | | | |
|---|---|---|---|
| 6,153,072 A | 11/2000 | Inoue et al. | |
| 6,200,445 B1 | 3/2001 | Yokota et al. | |
| 6,254,749 B1* | 7/2001 | Yokota | G01N 27/4074 204/424 |
| 6,338,783 B1 | 1/2002 | Inoue et al. | |
| 6,533,911 B1 | 3/2003 | Fujita et al. | |
| 6,645,361 B1 | 11/2003 | Bloemer et al. | |
| 8,133,370 B2 | 3/2012 | Roessler et al. | |
| 8,366,893 B2 | 2/2013 | Fujisaki et al. | |
| 2002/0023838 A1 | 2/2002 | Schneider et al. | |
| 2003/0205078 A1* | 11/2003 | Hasei | G01N 27/4074 73/23.31 |
| 2009/0114539 A1 | 5/2009 | Ziegler et al. | |

FOREIGN PATENT DOCUMENTS

| | | |
|---|---|---|
| EP | 2237029 A1 | 10/2010 |
| JP | 11-223617 A | 8/1999 |
| JP | 2000-28573 A | 1/2000 |
| JP | 3560316 B2 | 6/2004 |
| JP | 3566089 B2 | 6/2004 |
| JP | 4405643 B2 | 11/2009 |
| JP | 4827924 B2 | 9/2011 |
| JP | 4914447 B2 | 1/2012 |
| JP | 5323752 B2 | 7/2013 |

OTHER PUBLICATIONS

Norio Miura et al., "A review of mixed-potential type zirconia-based gas sensors," Ionics, May 2014, pp. 301-925, vol. 20, Springer, Germany.

The Notice of Reasons for Revocation of a Patent for the corresponding Japanese Patent No. 5883976 dispatched on Jan. 6, 2017.

The Opposition Notice for the corresponding Japanese Patent No. 5883976 dated Sep. 14, 2016.

The Communication pursuant to Article 94(3) EPC for the corresponding European application No. 15 178 072 3, dated Aug. 31, 2017.

* cited by examiner

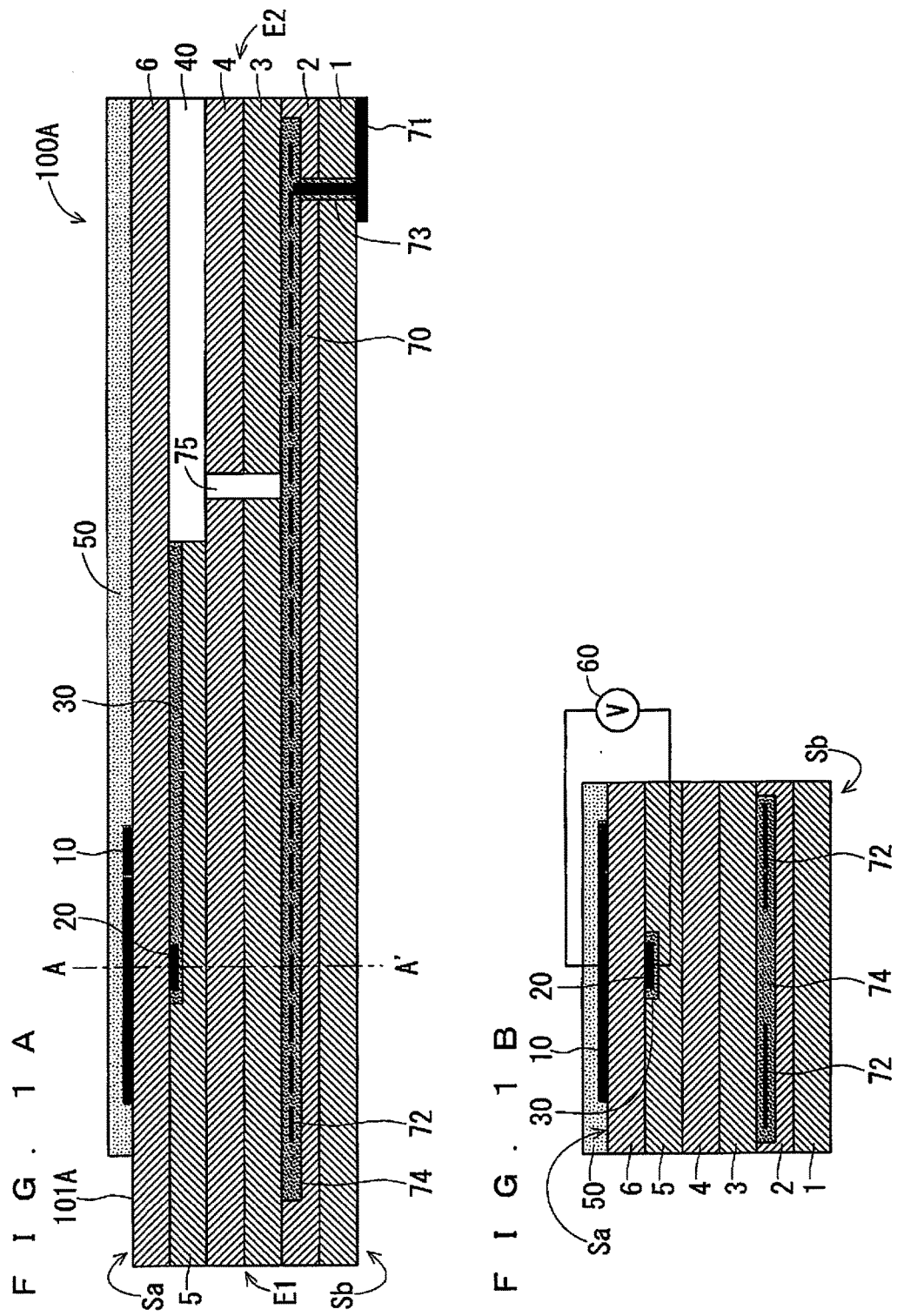

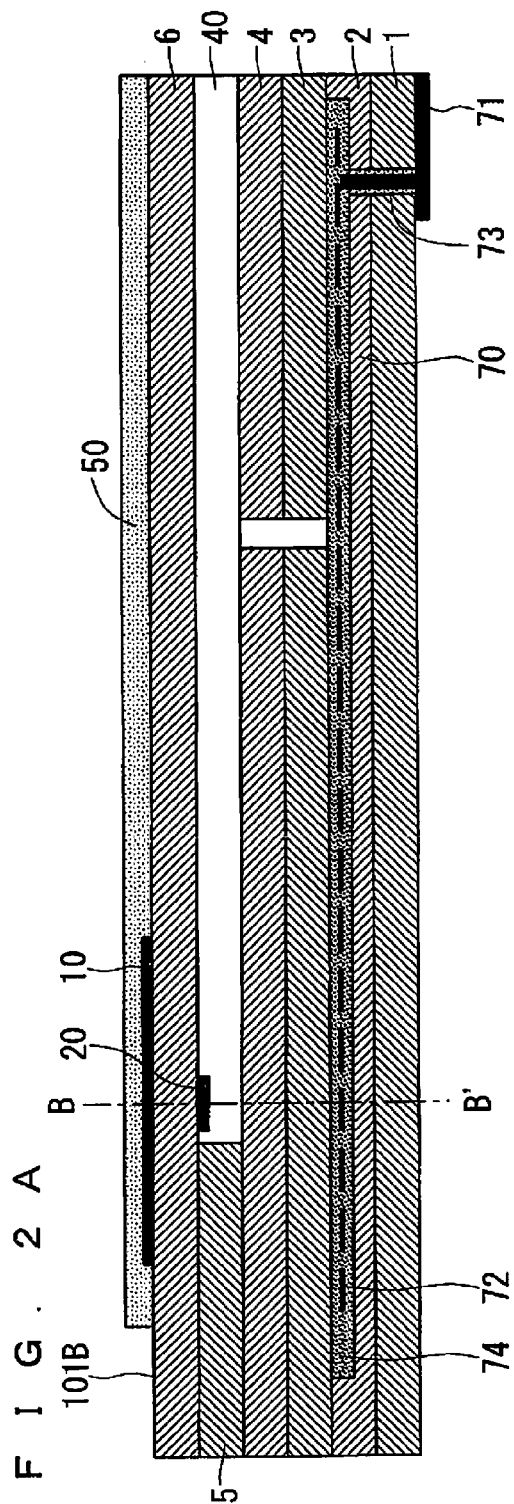
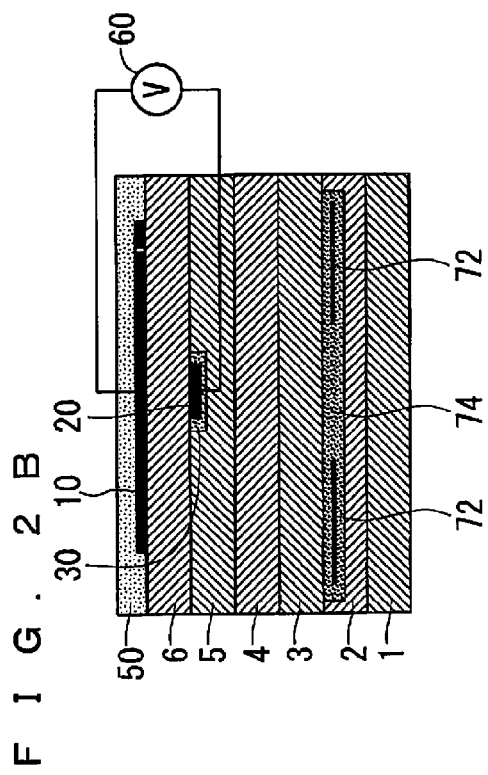

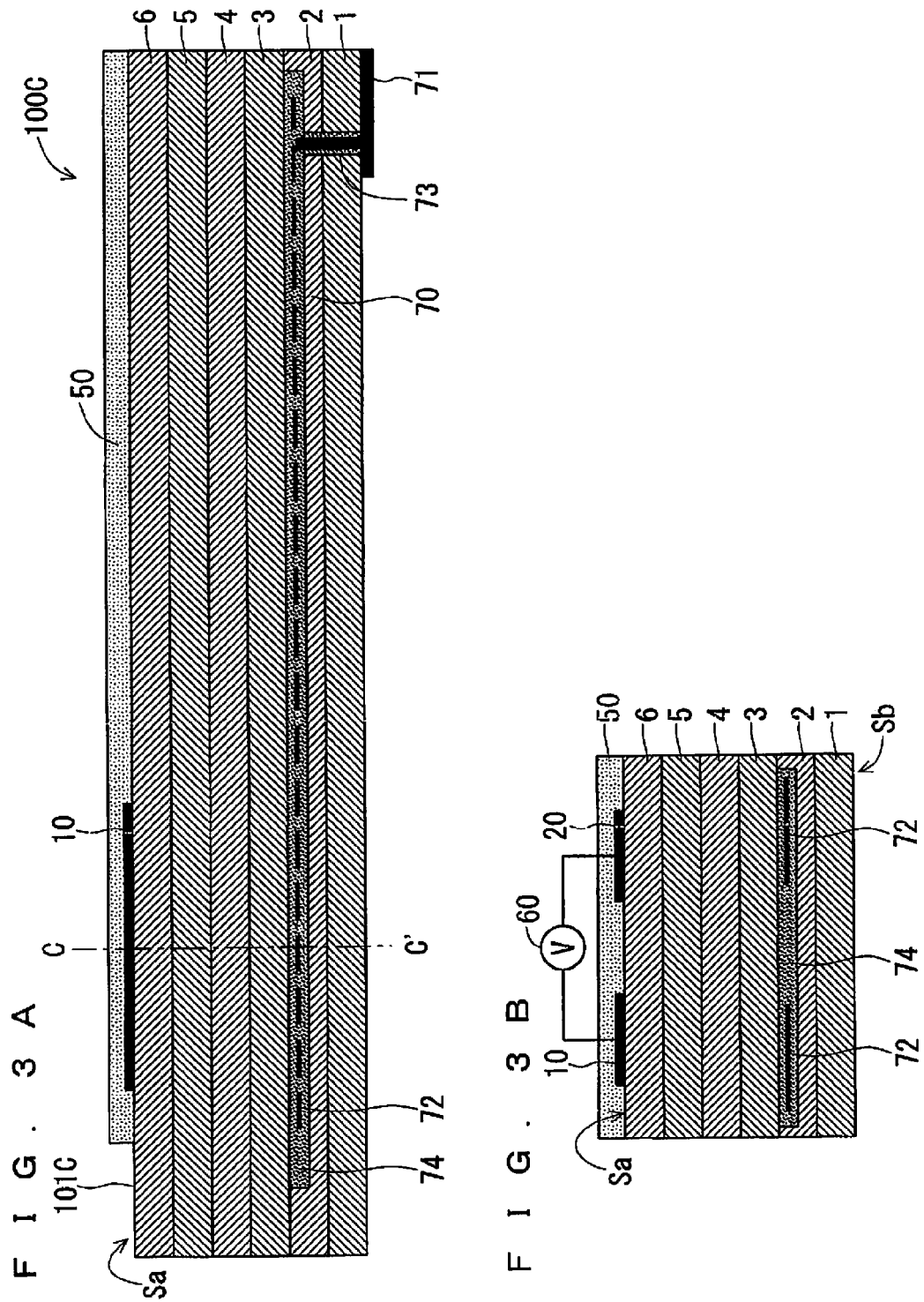

F I G . 5
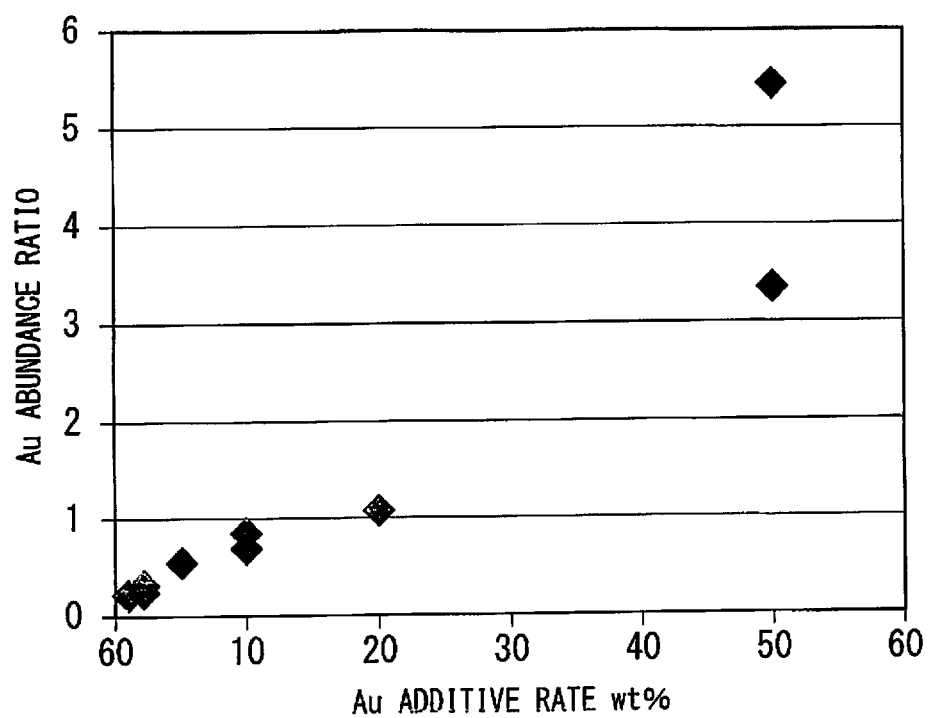

GAS SENSOR, METHOD OF PRODUCING CONDUCTIVE PASTE, AND METHOD OF MANUFACTURING GAS SENSOR

BACKGROUND OF THE INVENTION

Field of the Invention

The present invention relates to a gas sensor for sensing a hydrocarbon gas, and more particularly, to a sensing electrode of the gas sensor.

Description of the Background Art

Gas sensors that sense a predetermined gas component of a measurement gas to determine its concentration come in various types such as semiconductor gas sensor, catalytic combustion gas sensor, oxygen-concentration difference sensing gas sensor, limiting current gas sensor, and mixed-potential gas sensor (for example, see Japanese Patent Nos. 3566089, 4405643, 4914447, and 5323752). Some of these gas sensors are obtained by providing electrodes containing a noble metal as its main constituent to a sensor element mainly composed of ceramic being a solid electrolyte such as zirconia.

Japanese Patent Nos. 3566089 and 5323752 disclose a limiting current gas sensor including a sensor element formed of a solid electrolyte, which includes electrodes made of Pt—Au alloy as pumping electrodes.

Japanese Patent No. 4405643 discloses a gas sensor provided with a thin layer containing Pt or Au as its main constituent to compensate for the adhesion between a solid electrolyte and an electrode made of metal oxide and gold.

Japanese Patent No. 4914447 discloses a mixed-potential gas sensor including a first electrode formed through application of a Pt—Au paste and a second electrode formed through application of a Pt paste and Au plating.

In response to more stringent regulations on exhaust gas, there have recently been increasing demands for a diagnosis of failure in the performance of cleaning unburned hydrocarbon in an exhaust emission control system (TWC: three-way catalyst) of a gasoline engine and a diagnosis of failure in the performance of cleaning unburned hydrocarbon in an exhaust emission control system (DOC: diesel oxidation catalyst) of a diesel engine. These diagnoses require a gas sensor capable of sensing an unburned hydrocarbon gas and identifying its concentration.

The inventors of the present invention have made intensive studies to find out that in a sensing electrode made of Pt—Au alloy having an increased Au abundance ratio, the catalytic activation against a hydrocarbon gas is disabled, inducing a mixed potential having correlation with the concentration of the hydrocarbon gas. Such finding has led the inventors to a gas sensor capable of sensing a hydrocarbon gas with high sensitivity.

In the invention disclosed in Japanese Patent No. 4914447, the concentration of a gas component is determined on the premise that both of the first electrode and the second electrode have catalytic activation, although there may be a slight difference. In Japanese Patent No. 4405643, the relationship between the alloy composition of the electrode and detection sensitivity is not clear.

Japanese Patent No. 4405643 discloses that a pumping electrode for a limiting current gas sensor is made of Pt—Au alloy such that an Au abundance ratio is 0.01 or more and 0.3 or less, thereby increasing the selective decomposition ability for oxygen in the pumping electrode. Japanese Patent No. 4405643 also discloses that an Au abundance ratio exceeding 0.3 is not preferable because such a ratio increases electrode impedance. Japanese Patent No. 5323752, however, discloses or suggests nothing about a mixed-potential gas sensor (needless to say, about its sensing electrode as sell).

SUMMARY OF THE INVENTION

The present invention relates to a gas sensor for sensing a hydrocarbon gas and is particularly directed to the composition of its sensing electrode.

A mixed-potential gas sensor according to the present invention, which measures a concentration of a predetermined gas component of a measurement gas, includes: a sensor element mainly composed of an oxygen-ion conductive solid electrolyte; a sensing electrode for sensing the predetermined gas component, provided on a surface of the sensor element; and a reference electrode formed of a cermet including Pt and an oxygen-ion conductive solid electrolyte, provided in the sensor element. The gas sensor is configured to determine the concentration of the predetermined gas component on the basis of a potential difference between the sensing electrode and the reference electrode. The sensing electrode is formed of a cermet including a noble metal and an oxygen-ion conductive solid electrolyte. The noble metal comprises Pt and Au. An Au abundance ratio, which is an area ratio of a portion covered with the Au to a portion at which the Pt is exposed in a surface of noble metal particles forming the sensing electrode, is 0.3 or more.

According to the present invention, a gas sensor, which has excellent detection sensitivity to unburned hydrocarbon compared with a gas sensor including a sensing electrode containing only Pt as a noble metal component, can be achieved. The present invention therefore has an object to provide a gas sensor having excellent detection sensitivity to an unburned hydrocarbon gas.

BRIEF DESCRIPTION OF THE DRAWINGS

FIGS. 1A and 1B are schematic cross-sectional views schematically showing an example configuration of a gas sensor 100A according to a first embodiment of the present invention;

FIGS. 2A and 2B are schematic cross-sectional views schematically showing an example configuration of a gas sensor 100B that is a modification of the gas sensor 100A;

FIGS. 3A and 3B are schematic cross-sectional views schematically showing an example configuration of a gas sensor 100C according to a second embodiment of the present invention;

FIG. 5 shows an Au abundance ratio in a sensing electrode 10 formed of a conductive paste for forming a sensing electrode, which is plotted against an Au additive rate, where the conductive paste is produced through liquid-state Au mixing.

DESCRIPTION OF THE PREFERRED EMBODIMENTS

<First Embodiment>

Figure 4:
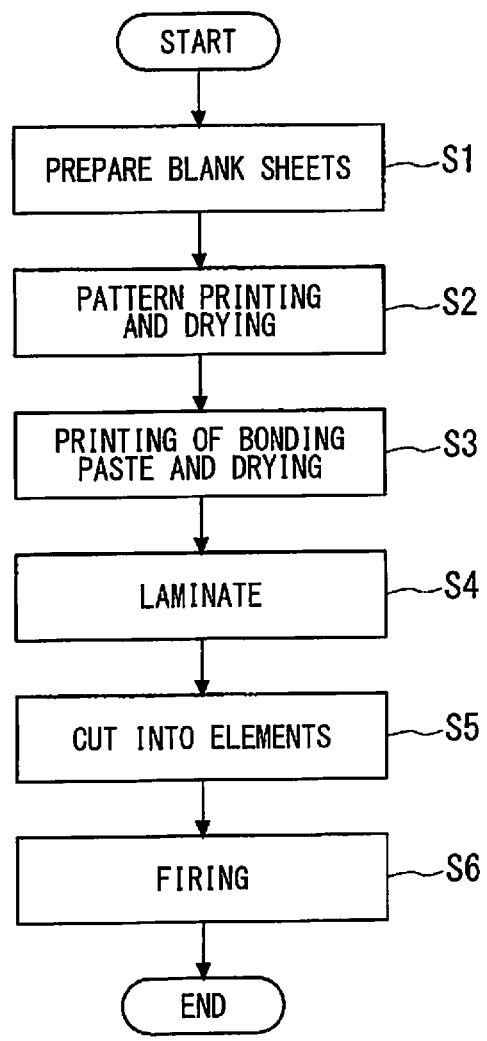
FIG. 4 shows the flow of a process of manufacturing sensor elements 101A to 101C.

FIGS. 1A and 1B are schematic cross-sectional views schematically showing an example configuration of a gas sensor 100A according to a first embodiment of the present invention. FIG. 1A is a vertical cross-sectional view of a sensor element 101A being a main component of the gas sensor 100A, which is taken along the longitudinal direction of the sensor element 101A. FIG. 1B is a view including a cross-section of the sensor element 101A vertical to the longitudinal direction taken along a position A-A' of FIG. 1A.

The gas sensor 100A according to this embodiment is a so-called mixed-potential gas sensor. Generally speaking, using a potential difference that occurs between a sensing electrode 10, which is provided on the surface of the sensor element 101A mainly composed of ceramic being an oxygen-ion conductive solid electrolyte such as zirconia ($ZrO_2$), and a reference electrode 20, which is provided inside the sensor element 101A, due to a difference in the concentration of a gas component being a measurement target between the portions near the electrodes on the basis of the principle of mixed potential, the gas sensor 100A determines the concentration of the gas component of a measurement gas.

More specifically, the gas sensor 100A preferably determines the concentration of an unburned hydrocarbon gas of a measurement gas, where the measurement gas is an exhaust gas present in an exhaust pipe of an internal combustion engine such as a diesel engine or a gasoline engine. In the specification, examples of the unburned hydrocarbon gas include carbon monoxide (CO) in addition to typical hydrocarbon gases (gases classified as hydrocarbon in terms of chemical formula) such as $C_2H_4$, $C_3H_6$, and n-C8. In the presence of a plurality of unburned hydrocarbon gases in a measurement gas, a potential difference occurring between the sensing electrode 10 and the reference electrode 20 has a value reflecting all the plurality of unburned hydrocarbon gases, and thus, a concentration value to be determined is also a total sum of the concentrations of the plurality of unburned hydrocarbon gases.

The sensor element 101A mainly includes a reference gas introduction layer 30, a reference gas introduction space 40, and a surface protective layer 50 in addition to the sensing electrode 10 and the reference electrode 20.

In this embodiment, the sensor element 101A has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101A additionally includes other components mainly between those layers or on an outer peripheral surface of the element. The solid electrolytes constituting those six layers are fully airtight. Such a sensor element 101A is manufactured by, for example, laminating ceramic green sheets corresponding to individual layers, which have been subjected to a predetermined process and printing of a circuit pattern, and further, by integrating the laminated layers through firing. The gas sensor 100A does not necessarily need to include the sensor element 101A formed as such a laminated body including six layers. The sensor element 101A may be formed as a laminated body having more or fewer layers or may not have a laminated structure.

In the following description, for convenience' sake, in FIGS. 1A and 1B, the surface located as the upper surface of the sixth solid electrolyte layer 6 is referred to as a front surface Sa of the sensor element 101A, and the surface located as the lower surface of the first solid electrolyte layer 1 is referred to as a rear surface Sb of the sensor element 101A. In the determination of the concentration of an unburned hydrocarbon gas of a measurement gas with the gas sensor 100A, a predetermined range starting from a distal end E1 being one end of the sensor element 101A, which includes at least the sensing electrode 10, is disposed in a measurement gas atmosphere, and the other portion including a base end E2 being the other end is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. Such a sensing electrode 10 is provided in a substantially rectangular shape in plan view at a position close to the distal end E1, being one end in the longitudinal direction of the sensor element 101A, on the front surface Sa of the sensor element 101A. The gas sensor 100A is placed such that, in its use, a portion where at least the sensing electrode 10 is provided is exposed to a measurement gas.

The catalytic activation of the sensing electrode 10 against an unburned hydrocarbon gas is disabled by preferably setting the composition of a Pt—Au alloy being its constituent material. That is, the decomposition reaction of an unburned hydrocarbon gas in the sensing electrode 10 is suppressed. In the gas sensor 100A, accordingly, the potential of the sensing electrode 10 selectively varies with respect to (has correlation with) the unburned hydrocarbon gas, in accordance with its concentration. In other words, the sensing electrode 10 is provided so as to have high dependence of potential on concentration for an unburned hydrocarbon gas while having low dependence of potential on concentration for components of other measurement gas. This will be described below in detail.

The reference electrode 20 is an electrode substantially rectangular in plan view, which is provided inside the sensor element 101A and serves a reference when the concentration of a measurement gas is determined. The reference electrode 20 is formed as a porous cermet electrode made of Pt and zirconia.

The reference gas introduction layer 30 is a layer made of porous alumina, which is provided inside the sensor element 101A to cover the reference electrode 20. The reference gas introduction space 40 is an internal space provided on the base end E2 side of the sensor element 101A. Air (oxygen), serving as a reference gas when the concentration of an unburned hydrocarbon gas is determined, is externally introduced into the reference gas introduction space 40.

The reference gas introduction space 40 and the reference gas introduction layer 30 are in communication with each other, and accordingly, in the use of the gas sensor 100A, the surroundings of the reference electrode 20 are always filled with air (oxygen) through the reference gas introduction space 40 and the reference gas introduction layer 30. During the use of the gas sensor 100A, therefore, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even if the sensing electrode 10 is exposed to the measurement gas.

In the case illustrated in FIGS. 1A and 1B, the reference gas introduction space 40 is provided in such a manner that part of the fifth solid electrolyte layer 5 is in communication with the outside on the base end E2 side of the sensor element 101A. The reference gas introduction layer 30 is provided so as to extend in the longitudinal direction of the sensor element 101A between the fifth solid electrolyte layer 5 and the sixth solid electrolyte layer 6. The reference electrode 20 is provided at a position below the center of gravity of the sensor element 101A in FIGS. 1A and 1B.

The surface protective layer 50 is a porous layer made of alumina, which is provided so as to cover at least the sensing electrode 10 on the front surface Sa of the sensor element 101A. The surface protective layer 50 is provided as an electrode protective layer that prevents or reduces the degradation of the sensing electrode 10 due to continuous exposure to a measurement gas during the use of the gas sensor 100A. In the case illustrated in FIGS. 1A and 1B, the surface protective layer 50 is provided so as to cover not only the sensing electrode 10 but also substantially all the portion of the front surface Sa of the sensor element 101A except for a predetermined range starting from the distal end E1.

As shown in FIG. 1B, the gas sensor 100A is equipped with a potentiometer 60 capable of measuring a potential difference between the sensing electrode 10 and the reference electrode 20. Although FIG. 1B schematically shows wiring between the potentiometer 60 and the sensing electrode 10 as well as the reference electrode 20, in an actual sensor element 101A, connection terminals (not shown) are provided correspondingly to the electrodes on the front surface Sa or the rear surface Sb on the base end E2 side, and wiring patterns (not shown), which connect the electrodes and their corresponding connection terminals, are formed on the front surface Sa and in the element. The sensing electrode 10 and the reference electrode 20 are electrically connected with the potentiometer 60 via the wiring patterns and the connection terminals. Hereinafter, the potential difference between the sensing electrode 10 and the reference electrode 20, measured by the potentiometer 60, is also referred to as a sensor output.

The sensor element 101A further includes a heater part 70, which performs temperature control of heating the sensor element 101A and maintaining the temperature of the sensor element 101A, to enhance the oxygen ion conductivity of the solid electrolyte. The heater part 70 includes a heater electrode 71, a heater 72, a through-hole 73, a heater insulating layer 74, and a pressure diffusion hole 75.

The heater electrode 71 is an electrode formed so as to come into contact with the rear surface Sb of the sensor element 101A (the lower surface of the first solid electrolyte layer 1 in FIGS. 1A and 1B). Connecting the heater electrode 71 with an external power source (not shown) enables power feeding from the outside to the heater part 70.

The heater 72 is an electric resistor provided inside the sensor element 101A. The heater 72, which is connected with the heater electrode 71 through the through-hole 73, generates heat by being fed power from the outside via the heater electrode 71 to heat the solid electrolytes forming the sensor element 101A and maintain their temperature.

In the case illustrated in FIGS. 1A and 1B, the heater 72 is buried while being vertically sandwiched between the second solid electrolyte layer 2 and the third solid electrolyte layer 3 so as to range from the base end E2 to the position below the sensing electrode 10 near the distal end E1. This enables the adjustment of the entire sensor element 101A to the temperature at which the solid electrolytes are activated.

The heater insulating layer 74 is an insulating layer made of an insulator such as alumina on the upper and lower surfaces of the heater 72. The heater insulating layer 74 is formed for the electrical insulation between the second solid electrolyte layer 2 and the heater 72 and for the electrical insulation between the third solid electrolyte layer 3 and the heater 72.

The pressure diffusion hole 75 is a part provided to penetrate the third solid electrolyte layer 3 and to be in communication with the reference gas introduction space 40, which is formed to mitigate an internal pressure rise associated with a temperature rise in the heater insulating layer 74.

To determine the concentration of an unburned hydrocarbon gas in a measurement gas using the gas sensor 100A having such a configuration, as described above, air (oxygen) is supplied to the reference gas introduction space 40, with the sensor element 101A in only a predetermined range, which starts from the distal end E1 and includes at least the sensing electrode 10, being disposed in a space in which a measurement gas is present, and with the sensor element 101A on the base end E2 side being disposed apart from the space. The sensor element 101A is heated by the heater 72 to an appropriate temperature from 400° C. to 800° C., preferably from 500° C. to 700° C., more preferably from 500° C. to 600° C.

In such a state, a potential difference occurs between the sensing electrode 10 exposed to the measurement gas and the reference electrode 20 disposed in the air. As described above, however, the potential of the reference electrode 20 disposed under the air (having a constant oxygen concentration) atmosphere is maintained at a constant potential, whereas the potential of the sensing electrode 10 selectively has concentration dependence on the unburned hydrocarbon gas of the measurement gas, and accordingly, their potential difference (sensor output) substantially has a value corresponding to the composition of the measurement gas present around the sensing electrode 10. Therefore, a certain functional relation (referred to as sensitivity characteristics) holds between the concentration of an unburned hydrocarbon gas and sensor output.

To actually determine the concentration of an unburned hydrocarbon gas, sensitivity characteristics are experimentally identified by measuring sensor output in advance with a plurality of different mixed gases, each of which has a known unburned hydrocarbon gas concentration, being measurement gases. In actual use of the gas sensor 100A, accordingly, the concentration of an unburned hydrocarbon gas of a measurement gas can be determined almost in real time by converting a sensor output, which varies from moment to moment in accordance with the concentration of an unburned hydrocarbon gas of a measurement gas, into the concentration of an unburned hydrocarbon gas on the basis of the sensitivity characteristics by a calculation processing unit (not shown).

<Modification of First Embodiment>

FIGS. 2A and 2B are schematic cross-sectional views schematically showing an example configuration of a gas sensor 100B being a modification of the gas sensor 100A. FIG. 2A is a vertical cross-sectional view of a sensor element 101B being a main component of the gas sensor 100B, which is taken along the longitudinal direction of the sensor element 101B. FIG. 2B is a view including a cross-section of the sensor element 101B vertical to the longitudinal direction at a position B-B' of FIG. 2A.

The gas sensor 100B is provided in such a manner that the reference gas introduction space 40 of the sensor element 101A of the gas sensor 100A is extended up to below the sensing electrode 10, whereas the reference gas introduction layer 30 is omitted and the reference electrode 20 is exposed to the reference gas introduction space 40. The other configuration is the same as that of the gas sensor 100A. A sensor output is accordingly generated as in the case of the gas sensor 100A. In other words, the gas sensor 100B is a so-called mixed potential gas sensor, similar to the gas sensor 100A.

The gas sensor 100B having the configuration described above can thus determine the concentration of an unburned hydrocarbon gas of a measurement gas by being provided with the sensor element 101B similarly to the gas sensor 100A and identifying its sensitivity characteristics in advance.

<Second Embodiment>

FIGS. 3A and 3B are schematic cross-sectional views schematically showing an example configuration of a gas sensor 100C according to a second embodiment of the present invention. FIG. 3A is a vertical cross-sectional view of a sensor element 101C being a main component of the gas sensor element 100C, which is taken along the longitudinal direction of the sensor element 101C. FIG. 3B is a view including a cross-section of the sensor element 101C vertical to the longitudinal direction at a position C-C' of FIG. 3A.

The gas sensor 100C is also a so-called mixed-potential gas sensor, similar to the gas sensors 100A and 100B. Unlike the sensor element 101A and the sensor element 101B, however, in the sensor element 101C of the gas sensor 100C, not only the sensing electrode 10 but also the reference electrode 20 is disposed on the front surface Sa of the sensor element 101C and is covered with the surface protective layer 50. The constituent material per se of each electrode is the same as those of the gas sensors 100A and 100B.

Meanwhile, the sensor element 101C does not include the reference gas introduction space 40 (and further, the reference gas introduction layer 30) and the pressure diffusion hole 75. The other components of the sensor element 101C are similar to those of the gas sensors 100A and 100B. In the case shown in FIGS. 3A and 3B, the sensing electrode 10 and the reference electrode 20 are provided at the same position in the longitudinal direction of the gas sensor 101C (see FIG. 3B), which is not necessarily required, and these electrodes may be disposed along the longitudinal direction.

To determine the concentration of an unburned hydrocarbon gas of a measurement gas using the gas sensor 100C having the configuration described above, unlike the gas sensors 100A and 100B, the sensor element 101C is disposed in such a manner that the reference electrode 20 as well as the sensing electrode 10 is exposed to the measurement gas. Although the sensing electrode 10 and the reference electrode 20 are accordingly exposed to the same atmosphere, the potential of the sensing electrode 10 selectively varies with respect to the concentration of an unburned hydrocarbon gas similarly to the gas sensors 100A and 100B because the constituent materials of the electrodes are the same as those of the gas sensors 100A and 100B. Meanwhile, unlike the sensing electrode 10, the catalytic activation of the reference electrode 20, which is formed as a porous cermet electrode of Pt and zirconia, is not reduced to a specific gas component. This results in that the sensing electrode 10 and the reference electrode 20 behave to gas components other than the unburned hydrocarbon gas in the same way. Also in the gas sensor 100C, thus, sensor output varies in accordance with an unburned hydrocarbon gas present in a measurement gas.

Therefore, the gas sensor 100C can also determine the concentration of an unburned hydrocarbon gas of a measurement gas by identifying sensitivity characteristics in advance, similarly to the gas sensors 100A and 100B.

<Process of Manufacturing Sensor Element>

Next, the process of manufacturing the sensor elements 101A to 101C will be described using a case in which the sensor elements have the layer structures illustrated in FIGS. 1A and 1B, 2A and 2B, and 3A and 3B. Generally speaking, the sensor elements 101A to 101C illustrated in FIGS. 1A and 1B, 2A and 2B, and 3A and 3B are manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

FIG. 4 shows a flow of the process of manufacturing the sensor elements 101A to 101C. In the manufacture of the sensor elements 101A to 101C, first, blank sheets (not shown) being green sheets having no pattern formed thereon are prepared (Step S1). Specifically, six blank sheets corresponding to the first to sixth solid electrolyte layers 1 to 6 are prepared. A blank sheet for forming the surface protective layer 50 is prepared as well. A plurality of sheet holes used for positioning in printing and lamination are provided in the blank sheets. Such sheet holes are formed in advance through, for example, punching by a punching machine. For a green sheet whose corresponding layer forming an internal space, a penetration corresponding to the internal space is provided in advance similarly through punching. All of the blank sheets corresponding to the sensor elements 101A to 101C need not to have the same thickness.

After the blank sheets corresponding to the respective layers are prepared, pattern printing and drying for forming various patterns are performed on the individual blank sheets (Step S2). Specifically, electrode patterns of, for example, the sensing electrode 10 and the reference electrode 20, the reference gas introduction layer 30, internal wiring (not shown), and the like are formed. A cut mark is printed on the first solid electrolyte layer 1, which is used as a reference of a cutting position for cutting a laminated body in a subsequent step.

Each pattern is printed by applying a paste for pattern formation, prepared in accordance with the characteristic required for each formation target, to the blank sheet using a known screen printing technique. Any known drying means is available for drying after printing.

This embodiment is characterized by the way of preparing a conductive paste used to form the sensing electrode 10, which will be described below in detail.

After the completion of pattern printing, printing and drying of a bonding paste are performed to laminate and bond the green sheets corresponding to the respective layers (Step S3). Any known screen printing technique is available for printing of a bonding paste, and any known drying means is available for drying after printing.

Subsequently, crimping is performed, in which the green sheets applied with an adhesive are laminated in a predetermined order, and the laminated green sheets are crimped on predetermined temperature and pressure conditions, to thereby form a laminated body (Step S4). Specifically, green sheets being lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body is obtained as described above, subsequently, a plurality of parts of the laminated body are cut out as individual units (referred to as element bodies) of the sensor elements 101A to 101C (Step S5). The cut out element bodies are fired under predetermined conditions, thereby generating the sensor elements 101A to 101C as described above (Step S6). In other words, the sensor elements 101A to 101C are produced by integrally firing the solid electrolyte layers and the electrodes. The firing temperature is preferably 1200° C. or higher and 1500° C. or lower (for example, 1365° C.). The integral firing in such a way provides satisfactory adhesion strength to the electrodes of the sensor elements 101A to 101C.

The thus obtained sensor elements 101A to 101C are housed in a predetermined housing and incorporated into main bodies (not shown) of the gas sensors 100A to 100C.

<Details of Electrode>

As described above, in the gas sensors 100A to 100C, the sensing electrode 10 is formed such that its catalytic activation against an unburned hydrocarbon gas is disabled. This is implemented by including gold (Au) in the sensing electrode 10 as a conductive component (a noble metal component), in addition to platinum (Pt) being a main constituent.

Specifically, the sensing electrode 10 is formed such that the abundance ratio of Au (Au abundance ratio) in the sensing electrode 10 is 0.3 or more. In such a case, the detection sensitivity becomes high compared with the case in which the sensing electrode 10 is formed as a cermet electrode of Pt and zirconia, similarly to the reference electrode 20.

In this specification, the Au abundance ratio means an area ratio of a portion covered with Au to a portion at which Pt is exposed in the surface of noble metal particles forming the sensing electrode 10. The Au abundance ratio is 1when the area of the portion at which Pt is exposed is equal to the area of the portion covered with Au. In this specification, an Au abundance ratio is calculated from a peak intensity of a peak detected for Au and Pt, obtained by X-ray photoelectron spectroscopy (XPS) using a relative sensitivity coefficient method.

For an Au abundance ratio of 0.3 or more, in the sensing electrode 10, Au is concentrated on the surface of noble metal particles forming the sensing electrode 10. In more detail, an Au-rich Pt—Au alloy is formed near the surface of Pt-rich Pt—Au alloy particles. When such a state is achieved, the catalytic activation in the sensing electrode 10 is preferably disabled, increasing the dependence of the potential of the sensing electrode 10 on the concentration of an unburned hydrocarbon gas.

The volume ratio between noble metal components and zirconia in the sensing electrode 10 may be about from 5:5 to 8:2.

For the gas sensors 100A to 100C to preferably exhibit their functions, the porosity of the sensing electrode 10 is preferably 10% or more and 30% or less, and the thickness of the sensing electrode 10 is preferably 5 μm or more. In particular, the porosity is more preferably 15% or more and 25% or less, and the thickness is more preferably 25 μm or more and 35 μm or less.

The plane size of the sensing electrode 10 may be appropriately set, and it suffices that, for example, the length in the longitudinal of the sensor element is about 2 mm to about 10 mm and the length perpendicular to the longitudinal direction is about from 1 mm to 5 mm.

Meanwhile, the reference electrode 20 may be formed to have a porosity of 10% or more and 30% or less and a thickness of 5 μm or more and 15 μm or less. The plane size of the reference electrode 20 may be smaller than that of the sensing electrode 10 as illustrated in FIGS. 1A and 1B or may be equal to that of the sensing electrode 10 as illustrated in FIG. 3B.

<Conductive Paste for Forming Sensing Electrode>

Next, a conductive paste used to form the sensing electrode 10 will be described. A conductive paste for forming a sensing electrode is produced by using an Au ion-containing liquid as an Au starting material and mixing the Au ion-containing liquid with powdered Pt, powdered zirconia, and a binder. Any binder, which can disperse other row material to the printable extent and vanishes through firing, may be appropriately selected. The production of a conductive paste in such a way is referred to as liquid-state Au mixing.

Here, the Au ion-containing liquid is obtained by dissolving a salt containing Au ion or an organometallic complex containing Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint that an impurity such as Na or K does not remain in the electrode, it is easy to handle, or it is likely to dissolve in the solvent. The solvent may be acetone, acetonitrile, or formamide as well as alcohols such as methanol, ethanol, or propanol.

Mixing can be performed by well-known means such as instillation. Although the obtained conductive paste contains Au in ionic (complex ionic) state, the sensing electrodes 10 formed in the sensor elements 101A to 101C obtained through the above-mentioned manufacturing process contain Au mainly as an elemental metal or as an alloy with Pt.

FIG. 5 shows an Au abundance ratio in the sensing electrode 10 formed of a conductive paste for forming a sensing electrode, which is plotted against an Au weight ratio (hereinafter, referred to as an Au additive rate) with respect to the weight of all the noble metal elements (a total weight of Pt and Au) of starting raw materials in a range of Au additive rate of 50 wt % or less, where the conductive paste is produced through liquid-state Au mixing.

FIG. 5 reveals, for an Au additive rate of 2 wt % or more, that the sensing electrode 10 having an Au abundance ratio of 0.3 or more can be manufactured and that an Au abundance ratio tends to increase with a higher Au additive rate. In other words, with the use of a conductive paste having an Au additive rate of 2 wt % or more, the sensing electrode 10 having an Au abundance ratio of 0.3 or more can be preferably formed. However, the Au additive rate is preferably set to 50 wt % or less because it is difficult to manufacture a highly conductive sensing electrode 10 at an Au additive rate exceeding 50 wt %.

Figure 6:
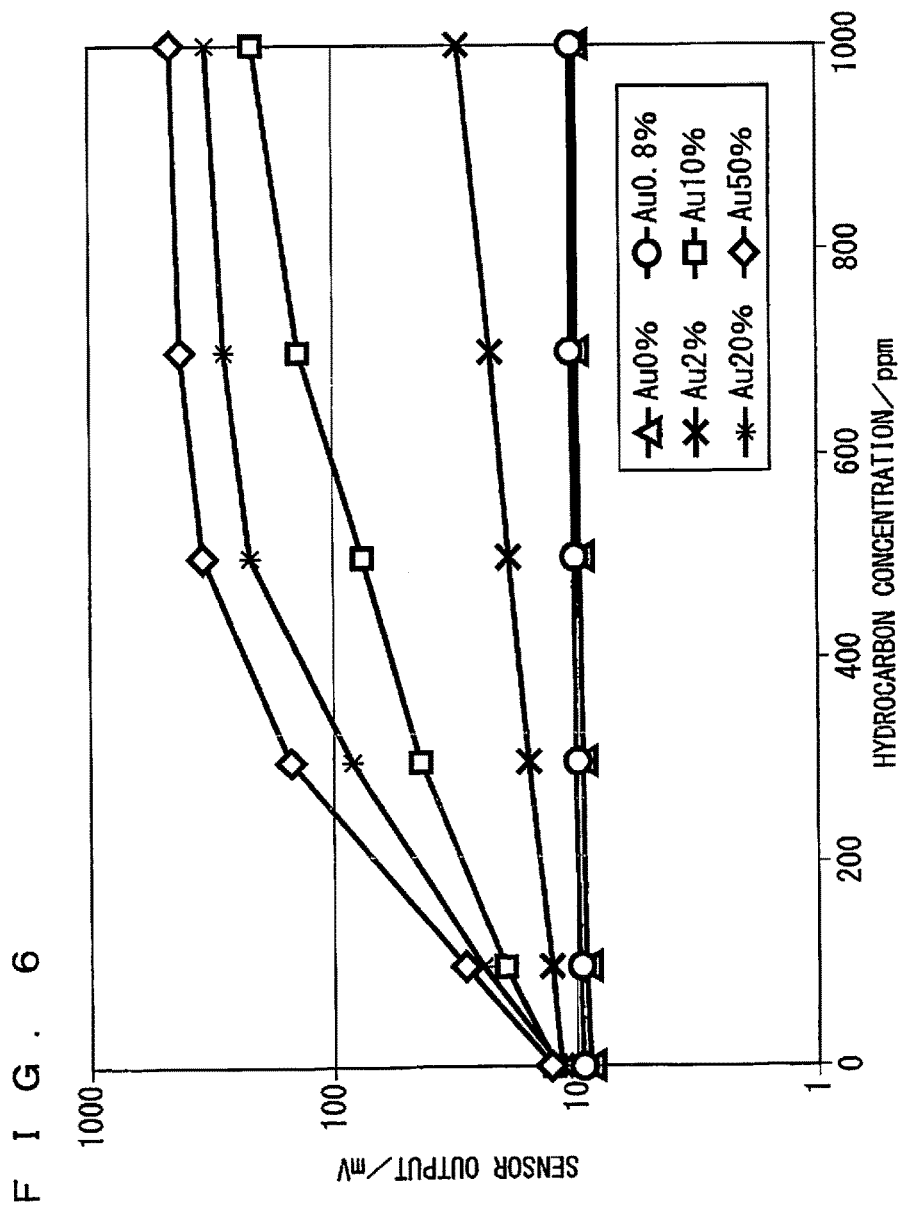
FIG. 6 shows the relationship between the concentration of a hydrocarbon gas and a sensor output for six types of gas sensors 100A including sensing electrodes 10 of six levels of Au additive rates.

FIG. 6 illustrates the relationship between the concentration of an unburned hydrocarbon gas (in FIG. 6, written as hydrocarbon concentration) and sensor output for six types of gas sensors 100A including the sensing electrodes 10 of six levels of Au additive rates, namely, 0 wt % (no addition), 0.8 wt %, 2 wt %, 10 wt %, 20 wt %, and 50 wt %. Herein, the sensor output of the vertical axis is represented on a logarithmic scale. The Au abundance ratios obtained at the respective Au additive rates are 0, about 0.2, about 0.3, about 0.7, about 1.1, and about 3.4 to 5.5 in order.

As the unburned hydrocarbon gas, $C_2H_4$ was used, and its concentration in a measurement gas was set to six levels, namely, 0 ppm, 100 ppm, 300 ppm, 500 ppm, 700 ppm, and 1000 ppm (excluding an Au additive rate of 0 wt %). The measurement gas contained 5 vol % water (water vapor) and 10 vol % oxygen in addition to an unburned hydrocarbon gas, and the remaining of the measurement gas was a nitrogen gas.

The porosity of the sensing electrode 10 was 20%, and the element temperature was 600° C.

As shown in FIG. 6, for Au additive rates of 0% and 0.8 wt % (respectively corresponding to Au abundance ratios of 0 and 0.2), sensor output hardly shows any dependence on hydrocarbon concentration and is also as small as about 10 mV with respect to $C_2H_4$=1000 ppm. Meanwhile, for Au additive rates of 2 wt % or more (Au abundance ratios of 0.3 or more), sensor output increased monotonously with respect to hydrocarbon concentration and showed 30 mV or more with respect to $C_2H_4$=1000 ppm. In particular, for Au additive rates of 10 wt % or more (Au abundance ratios of 0.7 or more), sensor output showed 200 mV or more with respect to $C_2H_4$=1000 ppm.

The results above mean that a gas sensor, which has excellent detection sensitivity to an unburned hydrocarbon compared with a gas sensor including a sensing electrode containing only Pt as a noble metal component, can be achieved by forming a sensing electrode for a sensor element as a cermet electrode of Pt containing Au so as to have an Au abundance ratio of 0.3 or more, that is, a Pt—Au alloy, and zirconia to disable the catalytic activation of the sensing electrode.

<Another Way of Producing Conductive Paste>

In the production of a conductive paste for forming a sensing electrode, the paste may be produced by using coated powder, which is obtained by coating powered Pt with Au, as starting raw materials, instead of producing the paste through liquid-state Au mixing as described above. In such a case, a conductive paste for a pump electrode in an inner space is produced by mixing the coated powder, powdered zirconia, and a binder. Here, the coated powder used in the above production may be obtained by covering the particle surface of powered Pt with an Au film or applying Au particles to Pt powder particles.

Also in this case, the sensing electrode 10 having an Au abundance ratio of 0.3 or more can be preferably formed.

The invention claimed is:

1. A mixed-potential type hydrocarbon gas sensor that measures a concentration of a hydrocarbon gas of a measurement gas, said sensor comprising:
    a sensor element mainly composed of an oxygen-ion conductive solid electrolyte;
    a sensing electrode for sensing said hydrocarbon gas, provided on a surface of said sensor element; and
    a reference electrode formed of a cermet including Pt and an oxygen-ion conductive solid electrolyte, provided in said sensor element, wherein
    said gas sensor is configured to determine the concentration of said hydrocarbon gas on the basis of a potential difference between said sensing electrode and said reference electrode,
    said sensing electrode is formed of a cermet including a noble metal and an oxygen-ion conductive solid electrolyte,
    said noble metal comprises Pt and Au, and
    an Au abundance ratio in an entirety of the sensing electrode, which is an area ratio of a portion covered with said Au to a portion at which said Pt is exposed in a surface of noble metal particles forming said sensing electrode, is 0.3 or more and less than or equal to 5.5.

2. The mixed-potential type hydrocarbon gas sensor according to claim 1, wherein the Au abundance ratio is 0.7 or more and less than or equal to 5.5.

3. The mixed-potential type hydrocarbon gas sensor according to claim 1, further comprising an electrode protective layer being a porous layer that covers at least said sensing electrode.

4. The mixed-potential type hydrocarbon gas sensor according to claim 1, wherein
    said sensor element further includes a reference gas introduction space separated from a space in which said measurement gas is present, into which a reference gas is introduced, and
    said reference electrode is placed under an atmosphere of said reference gas.

5. The mixed-potential type hydrocarbon gas sensor according to claim 4, wherein
    said sensor element further includes a reference gas introduction layer being a porous layer that is in communication with said reference gas introduction space, and
    said reference electrode is covered with said reference gas introduction layer.

6. The mixed-potential type hydrocarbon gas sensor according to claim 4, wherein said reference electrode is exposed to said reference gas introduction space.

7. The mixed-potential type hydrocarbon gas sensor according to claim 1, wherein said sensing electrode and said reference electrode are disposed on the surface of said sensor element.

8. The mixed-potential type hydrocarbon gas sensor according to claim 7, wherein said sensing electrode and said reference electrode are covered with an electrode protective layer.

9. A method of producing a conductive paste, said conductive paste being used to form a sensing electrode of a mixed-potential type hydrocarbon gas sensor that measures a concentration of a hydrocarbon gas of a measurement gas, said method comprising the steps of:
    preparing starting raw materials; and
    mixing said starting raw materials, wherein
    at least powdered Pt and an ion-containing liquid including a salt containing Au ion or an organometallic complex containing Au ion dissolved in a solvent are prepared as said starting raw materials, and
    said starting raw materials are mixed such that a weight ratio of said Au in a noble metal component of said conductive paste is 2 wt % or more and 50 wt % or less, wherein
    said mixed-potential type hydrocarbon gas sensor comprises:
        a sensor element mainly composed of an oxygen-ion conductive solid electrolyte;
        said sensing electrode for sensing said hydrocarbon gas, provided on a surface of said sensor element; and
        a reference electrode formed of a cermet including Pt and an oxygen-ion conductive solid electrolyte, provided in said sensor element,
    said mixed-potential type hydrocarbon gas sensor is configured to determine the concentration of said hydrocarbon gas on the basis of a potential difference between said sensing electrode and said reference electrode, said sensing electrode is formed of a cermet including a noble metal and an oxygen-ion conductive solid electrolyte, said noble metal comprises Pt and Au, and an Au abundance ratio, which is an area ratio of a portion covered with said Au to a portion at which said Pt is exposed in a surface of noble metal particles forming said sensing electrode, is 0.3 or more.

10. A method of producing a conductive paste, said conductive paste being used to form a sensing electrode of a mixed-potential type hydrocarbon gas sensor that measures a concentration of a hydrocarbon gas of a measurement gas, said method comprising the steps of:

preparing starting raw materials; and mixing said starting raw materials, wherein at least coated powder containing powered Pt coated with Au is prepared as said starting raw materials, and said starting raw materials are mixed such that a weight ratio of said Au in a noble metal component of said conductive paste is 2 wt % or more and 50 wt % or less, said gas sensor comprises:
    a sensor element mainly composed of an oxygen-ion conductive solid electrolyte;
    said sensing electrode for sensing said hydrocarbon gas, provided on a surface of said sensor element; and
    a reference electrode formed of a cermet including Pt and an oxygen-ion conductive solid electrolyte, provided in said sensor element, said mixed-potential type hydrocarbon gas sensor is configured to determine the concentration of said hydrocarbon gas on the basis of a potential difference between said sensing electrode and said reference electrode, said sensing electrode is formed of a cermet including a noble metal and an oxygen-ion conductive solid electrolyte, said noble metal comprises Pt and Au, and an Au abundance ratio, which is an area ratio of a portion covered with said Au to a portion at which said Pt is exposed in a surface of noble metal particles forming said sensing electrode, is 0.3 or more.

11. A method of manufacturing a mixed-potential type hydrocarbon gas sensor that measures a concentration of a hydrocarbon gas of a measurement gas, comprising the steps of:
    a) preparing a conductive paste;
    b) preparing a plurality of green sheets each including said solid electrolyte;
    c) applying said conductive paste to part of said plurality of green sheets to form a pattern of a sensing electrode;
    d) creating a laminated body of said plurality of green sheets including a green sheet having the pattern of said sensing electrode formed thereon; and
    e) firing said laminated body to fire said sensing electrode integrally with said solid electrolytes, wherein
said step a) comprises the steps of:
    a-1) preparing starting raw materials; and
    a-2) mixing said starting raw materials,
at least powdered Pt and an ion-containing liquid including a salt containing Au ion or an organometallic complex containing Au ion dissolved in a solvent are prepared as said starting raw materials, said starting raw materials are mixed such that a weight ratio of said Au in a noble metal component of said conductive paste is 2 wt % or more and 50 wt % or less, said mixed-potential type hydrocarbon gas sensor comprises:
    a sensor element mainly composed of an oxygen-ion conductive solid electrolyte;
    said sensing electrode for sensing said hydrocarbon gas, provided on a surface of said sensor element; and
    a reference electrode formed of a cermet including Pt and an oxygen-ion conductive solid electrolyte, provided in said sensor element, said mixed-potential type hydrocarbon gas sensor is configured to determine the concentration of said hydrocarbon gas on the basis of a potential difference between said sensing electrode and said reference electrode, said sensing electrode is formed of a cermet including a noble metal and an oxygen-ion conductive solid electrolyte, said noble metal comprises Pt and Au, and an Au abundance ratio, which is an area ratio of a portion covered with said Au to a portion at which said Pt is exposed in a surface of noble metal particles forming said sensing electrode, is 0.3 or more.

12. A method of manufacturing a mixed-potential type hydrocarbon gas sensor that measures a concentration of a hydrocarbon gas of a measurement gas, comprising the steps of:
    a) preparing a conductive paste;
    b) preparing a plurality of green sheets each including a solid electrolyte;
    c) applying said conductive paste to part of said plurality of green sheets to form a pattern of a sensing electrode;
    d) creating a laminated body of said plurality of green sheets including a green sheet having the pattern of said sensing electrode formed thereon; and
    e) firing said laminated body to fire said sensing electrode integrally with said solid electrolytes, wherein
said step a) comprises the steps of:
    a-1) preparing starting raw materials; and
    a-2) mixing said starting raw materials,
at least coated powder containing powered Pt coated with Au is prepared as said starting raw materials, said starting raw materials are mixed such that a weight ratio of said Au in a noble metal component of said conductive paste is 2 wt % or more and 50 wt % or less, said mixed-potential type hydrocarbon gas sensor comprises:
    a sensor element mainly composed of an oxygen-ion conductive solid electrolyte;
    said sensing electrode for sensing said hydrocarbon gas, provided on a surface of said sensor element; and
    a reference electrode formed of a cermet including Pt and an oxygen-ion conductive solid electrolyte, provided in said sensor element, said gas sensor is configured to determine the concentration of said hydrocarbon gas on the basis of a potential difference between said sensing electrode and said reference electrode, said sensing electrode is formed of a cermet including a noble metal and an oxygen-ion conductive solid electrolyte, said noble metal comprises Pt and Au, and
an Au abundance ratio, which is an area ratio of a portion covered with said Au to a portion at which said Pt is exposed in a surface of noble metal particles forming said sensing electrode, is 0.3 or more.

13. The mixed-potential type hydrocarbon gas sensor according to claim 1, further comprising
a potentiometer configured to measure the potential difference between said sensing electrode and said reference electrode.

14. The mixed-potential type hydrocarbon gas sensor according to claim 1, wherein
the sensor element is provided on a surface of an outermost solid electrolyte layer of the sensor element.

15. The mixed-potential type hydrocarbon gas sensor according to claim 1, wherein
a weight ratio of said Au with respect to a total weight of noble metal elements in the sensing electrode is 2 wt % or more.

* * * * *